(12) United States Patent
Tao et al.

(10) Patent No.: US 11,958,186 B2
(45) Date of Patent: Apr. 16, 2024

(54) STRUCTURAL MEMBER OF ROBOT, ROBOT, AND ASSOCIATED MANUFACTURING METHOD

(71) Applicant: ABB Schweiz AG, Baden (CH)

(72) Inventors: Zhiqiang Tao, Beijing (CN); Hao Gu, Shanghai (CN); Shanghua Li, Västerås (SE); Cuicui Su, Beijing (CN); Weidong Zhou, Beijing (CN); Jiansheng Chen, Beijing (CN); Shaobo Xie, Beijing (CN)

(73) Assignee: ABB SCHWEIZ AG, Baden (CH)

( * ) Notice: Subject to any disclaimer, the term of this patent is extended or adjusted under 35 U.S.C. 154(b) by 782 days.

(21) Appl. No.: 17/014,093

(22) Filed: Sep. 8, 2020

(65) Prior Publication Data
US 2020/0398444 A1 Dec. 24, 2020

Related U.S. Application Data

(63) Continuation of application No. PCT/CN2018/103367, filed on Aug. 30, 2018.

(51) Int. Cl.
*B25J 19/00* (2006.01)
*A61L 2/238* (2006.01)
(Continued)

(52) U.S. Cl.
CPC ......... *B25J 19/0087* (2013.01); *A61L 2/238* (2013.01); *B25J 9/0012* (2013.01);
(Continued)

(58) Field of Classification Search
CPC .. B25J 9/0012; B25J 11/0045; B25J 19/0087; A61L 2/238; B29C 45/0001; B29C 64/106; B33Y 80/00
See application file for complete search history.

(56) References Cited

U.S. PATENT DOCUMENTS 4,911,898 A * 3/1990 Hagiwara ............... A46D 1/00
423/DIG. 25
5,195,388 A * 3/1993 Zona ...................... B25J 9/08
310/71

(Continued)

FOREIGN PATENT DOCUMENTS

CN 1378901 A 11/2002
CN 1680494 A 10/2005
(Continued)

OTHER PUBLICATIONS

Sathishkumar T, Naveen J, Satheeshkumar S. Hybrid fiber reinforced polymer composites—a review. Journal of Reinforced Plastics and Composites. 2014;33(5):454-471. doi:10.1177/0731684413516393 (Year: 2014).*

(Continued)

*Primary Examiner* — Joseph Brown
(74) *Attorney, Agent, or Firm* — Greenberg Traurig, LLP

(57) ABSTRACT

Structural members and methods for manufacturing a plastic-based, bulk, antimicrobial structural member of a robot. Such bulk antimicrobial plastic solution can meet the hygienic requirement and the mechanical performance requirement of a structural member of a robot simultaneously. Meanwhile, it may reduce the overall weight of the robot.

23 Claims, 2 Drawing Sheets

(51) Int. Cl.
  *B25J 9/00* (2006.01)
  *B29C 45/00* (2006.01)
  *B29C 64/106* (2017.01)
  *B33Y 80/00* (2015.01)

(52) U.S. Cl.
  CPC ........ *B29C 45/0001* (2013.01); *B29C 64/106* (2017.08); *B33Y 80/00* (2014.12)

(56) References Cited

U.S. PATENT DOCUMENTS

| | | | | |
|---|---|---|---|---|
| 5,919,554 | A | * | 7/1999 | Watterson, III ........ A01N 25/34 428/394 |
| 6,485,735 | B1 | * | 11/2002 | Steen ..................... A61B 18/14 424/443 |

FOREIGN PATENT DOCUMENTS

| | | | |
|---|---|---|---|
| CN | 102597132 | A | 7/2012 |
| CN | 102892824 | A | 1/2013 |
| CN | 105764655 | A | 7/2016 |
| CN | 107961075 | A | 4/2018 |
| DE | 202010007727 | U1 | 9/2010 |
| EP | 0988939 | A1 | 3/2000 |
| EP | 2631061 | A1 | 8/2013 |
| FR | 3059239 | A3 | 6/2018 |
| JP | 2008030186 | A | 2/2008 |
| JP | 2010115732 | A | 5/2010 |
| WO | 2006032603 | A1 | 3/2006 |

OTHER PUBLICATIONS

Wikipedia contributors. (Jul. 31, 2018). Fibre-reinforced plastic. In Wikipedia, The Free Encyclopedia. Retrieved 14:47, Aug. 10, 2023, from https://en.wikipedia.org/w/index.php?title=Fibre-reinforced_plastic&oldid=852806586 (Year: 2018).*

Wikipedia contributors. (Aug. 29, 2018). Zeolite. In Wikipedia, The Free Encyclopedia. Retrieved 15:14, Aug. 10, 2023, from https://en.wikipedia.org/w/index.php?title=Zeolite&oldid=857127050 (Year: 2018).*

Gebretinsae Yeabyo Nigussie, "Antibacterial Activity of Ag-Doped $TiO_2$ and Ag-Doped ZnO Nanoparticles", International Journal of Photoenergy, vol. 2018, Article ID 5927485, 7 pages, 2018. https://doi.org/10.1155/2018/5927485 (Year: 2018).*

Wikipedia contributors. (Jul. 6, 2018). Coupling reaction. In Wikipedia, The Free Encyclopedia. Retrieved 16:28, Aug. 10, 2023, from https://en.wikipedia.org/w/index.php?title=Coupling_reaction&oldid=849123927 (Year: 2018).*

Porosa, Lukas. (2017). UV-Curable Contact Active Benzophenone Terminated Quaternary Ammonium Antimicrobials for Applications in Polymer Plastics and Related Devices. ACS Applied Materials & Interfaces. 9. 10.1021/acsami.7b07363. (Year: 2017).*

Intellectual Property Office of the P.R. China, International Search Report & Written Opinion issued in corresponding Application No. PCT/CN2018/103367, dated Jan. 23, 2019, 9 pp.

* cited by examiner

STRUCTURAL MEMBER OF ROBOT, ROBOT, AND ASSOCIATED MANUFACTURING METHOD

FIELD

Embodiments of present disclosure generally relate to an improvement of a robot, and more specifically, to a structural member of a robot, a robot comprising the structural member, and associated manufacturing method.

BACKGROUND

Structural members (or structural parts) are the key components for robots, and especially for an industrial robot. From one aspect, such structural members are normally designed to bear certain mechanical loadings, such as certain mechanical torques and weights. From another aspect, with the emerging applications of robots in some particular fields, such as food, beverage and heath care, a more rigorous hygienic standard is always required compared to previous industrial robots.

For example, in some applications, the material of the robot might be required to prevent bacteria ingress, survival, growth and reproduction on its exposed surface of the industrial robot. For some applications where the robots are operated in corrosive environments, the materials for all exposed surfaces may additionally be required to exhibit a good resistance to corrosion.

Some hygienic and corrosion-resistant treatments have been proposed and applied in some robot designs. As an example, EP0988939A1 discloses an industrial robot where antimicrobial treatment is applied on an outer surface of mechanical portion by resin coating, without changing the raw materials of the mechanical portion. In those solutions, the lifetime and endurance of functional coating shall be concerned, especially for crack and peeling resistant. Meanwhile, due to the unmodified conventional raw material (such as iron), the robot might still be heavy.

As another example, WO2006/032603A1 discloses a griping device that comprises an antimicrobial agent providing the surface of the gripping device an antimicrobial effect. In this design, the antimicrobial agent is either evenly distributed in the gripping device, or arranged as a coating on the gripping device, or arranged as a modified surface on the gripping device. However, such antimicrobial treatment is only provided for griping device, but not the structural member of the robot that can bear the mechanical loadings.

SUMMARY

Embodiments of the present disclosure provide a plastic-based, bulk, antimicrobial structural member of a robot. Such bulk antimicrobial plastic solution can meet the hygienic requirement and the mechanical performance requirement of a structural member of a robot simultaneously. Meanwhile, it may reduce the overall weight of the robot.

In a first aspect, a structural member of a robot is provided. The structural member is adapted to be exposed to environment and bear a mechanical load, and comprises: a plastic matrix; and an antimicrobial additive mixed with the plastic matrix.

In some embodiments, the structural member comprises: an arm, a wrist, a translation axle, or a rotary axle of the robot.

In some embodiments, the structural member is formed from the plastic matrix and the antimicrobial additive by injection moulding, machining, or 3D printing.

In some embodiments, the plastic matrix is made of a fiber reinforced plastic.

In some embodiments, the fiber reinforced plastic is selected from at least one of: a short fiber reinforced plastic; a long fiber reinforced plastic; and a fiber reinforced plastic with a fiber content larger than 30 wt %.

In some embodiments, the fiber reinforced plastic with fiber content larger than 30% is a fiber reinforced plastic with a fiber content larger than 40%.

In some embodiments, the antimicrobial additive is a first type of antimicrobial additive, and wherein the first type of antimicrobial additive is a metal ion type and comprises a metal ion comprising silver ion and copper ion.

In some embodiments, the first type of antimicrobial additive further comprises a first carrier comprising zeolite and glass, for coupling with the metal ion.

In some embodiments, a content of the first type of antimicrobial additive in the structural member is in a range of 0.5-5 wt %.

In some embodiments, the antimicrobial additive is a second type of antimicrobial additive, and wherein the second type of antimicrobial additive is an inorganic oxide type and comprises a photo catalyst comprising zinc oxide and titanium dioxide.

In some embodiments, the second type of antimicrobial additive further comprises a metal ion as a doping of the photo catalyst.

In some embodiments, the second type of antimicrobial additive further comprises a coupling agent to couple the photo catalyst to the plastic matrix.

In some embodiments, a content of the second type of antimicrobial additive in the structural member is in a range of 0.5-5 wt %.

In some embodiments, the antimicrobial additive is a third type of antimicrobial additive, and wherein the third type of antimicrobial additive is an organic type and comprises at least one of: quaternary ammonium salt, peptide, low molecular weight agents, and antimicrobial polymers.

In some embodiments, a content of the third type of antimicrobial additive in the structural member is in a range of 0.5-5 wt %.

In a second aspect, a method for manufacturing a structural member of a robot is provided. The method comprises: preparing a plastic matrix; and mixing an antimicrobial additive with the plastic matrix to form, by injection moulding, machining, or 3D printing, the structural member that is adapted to expose to an environment and bear a mechanical load.

In some embodiments, preparing the plastic matrix comprises: preparing the plastic matrix from a fiber reinforced plastic.

In some embodiments, the fiber reinforced plastic is selected from at least one of: a short fiber reinforced plastic; a long fiber reinforced plastic; and a fiber reinforced plastic with a fiber content larger than 30%.

In some embodiments, the fiber reinforced plastic with a fiber content larger than 30% is a fiber reinforced plastic with a fiber content larger than 40%.

In some embodiments, the method further comprises: forming the antimicrobial additive having a form of a master batch by extruder compounding.

In some embodiments, the antimicrobial additive is a first type of antimicrobial additive, and the first type of antimicrobial additive is a metal ion type and comprises a metal ion comprising silver ion and copper ion.

In some embodiments, the first type of antimicrobial additive further comprises a first carrier comprising zeolite and glass, for coupling with the metal ion.

In some embodiments, a content of the first type of antimicrobial additive in the structural member is in a range of 0.5-5 wt %.

In some embodiments, the antimicrobial additive is a second type of antimicrobial additive, and the second type of antimicrobial additive is an inorganic oxide type and comprises a photo catalyst comprising zinc oxide and titanium dioxide.

In some embodiments, the second type of antimicrobial additive further comprises a metal ion as doping of the photo catalyst.

In some embodiments, the second type of antimicrobial additive further comprises a coupling agent to couple the photo catalyst to the plastic matrix.

In some embodiments, a content of the second type of antimicrobial additive in the structural member is in a range of 0.5-5 wt %.

In some embodiments, the antimicrobial additive is a third type of antimicrobial additive, and wherein the third type of antimicrobial additive is an organic type and comprises at least one of: quaternary ammonium salt, peptide, low molecular weight agents, and antimicrobial polymers.

In some embodiments, a content of the third type of antimicrobial additive in the structural member is in a range of 0.5-5 wt %.

In some embodiments, the structural member comprises: an arm, a wrist, a translation axle, or a rotary axle of the robot.

In a third aspect, a robot is provided. The robot comprises at least one structural member according to the first aspect of the present disclosure.

DESCRIPTION OF DRAWINGS

Drawings described herein are provided to further explain the present disclosure and constitute a part of the present disclosure. The example embodiments of the disclosure and the explanation thereof are used to explain the present disclosure, rather than to limit the present disclosure improperly.

Throughout the drawings, the same or similar reference symbols are used to indicate the same or similar elements.

DETAILED DESCRIPTION OF EMBODIMENTS

Figure 1:
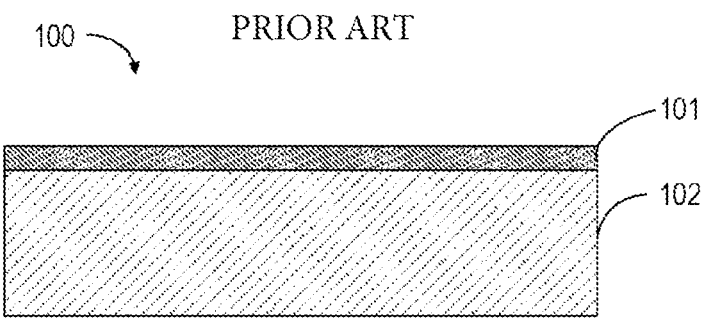
FIG. 1 illustrates a side view of a conventional structural member of a robot coated with a coating layer.

Principles of the present disclosure will now be described with reference to several example embodiments shown in the drawings. Though example embodiments of the present disclosure are illustrated in the drawings, it is to be understood that the embodiments are described only to facilitate those skilled in the art in better understanding and thereby achieving the present disclosure, rather than to limit the scope of the disclosure in any manner.

As used herein, the term "includes" and its variants are to be read as open terms that mean "includes, but is not limited to." The term "based on" is to be read as "based at least in part on." The term "one embodiment" and "an embodiment" are to be read as "at least one embodiment." The term "another embodiment" is to be read as "at least one other embodiment." The terms "first," "second," and the like may refer to different or same objects. Other definitions, explicit and implicit, may be included below. A definition of a term is consistent throughout the description unless the context clearly indicates otherwise.

For majority of conventional industrial robots, most of their arms are made by metallic material. Among them, stainless steel is a promising material due to its excellent mechanical performance and corrosion protection properties. Meanwhile, by means of the smooth surface and through timely cleaning maintenance (by such as, wipe down or wash down method), such stainless steel based solution can meet some hygienic requirements. However, it is not a light weight solution due to its relatively high density of 7.7-8.0 g/cm$^3$.

Surface treatment is another conventional solution to realize the antimicrobial robot. FIG. 1 schematically illustrates a side view of a conventional structural arm 100 of a robot coated with a coating layer. In this case, the exposed surface of robot arm 101 can be coated by special coating layer 102 containing antimicrobial agent. The coating-based solution can meet the requirements of corrosion resistant and antimicrobial for general industrial robot. However, the lifetime and endurance of functional coating should be concerned, especially for potential crack or peeling that may occur on the coating layer.

Figure 2:
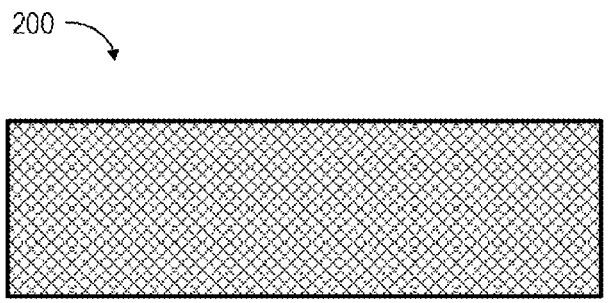
FIG. 2 illustrates a side view of a structural member of a robot, in accordance with an embodiment of the present disclosure.

Unlike the above mentioned stainless-based or coating-based solutions, embodiments of the present disclosure provide a plastic-based, bulk, and antimicrobial solution for use in the structural member of a robot. FIG. 2 illustrates a side view of the structural member in accordance with various embodiments of the present disclosure. Although the structural member throughout the present disclosure will be described with a reference of a robot arm, it is to be understood that the same technical solution can also be applied to other types of structural members, such as wrists, translation axles, or rotary axles of a robot that can bear a predefined mechanical load.

As illustrated in FIG. 2, the structural member 200 according to various embodiments of the present disclosure generally comprises a plastic matrix and an antimicrobial additive mixed with the plastic matrix. In other words, in the present disclosure, traditional metal for robot arms is replaced by the plastic-based material with the mixed antimicrobial additive. In this way, antimicrobial additives can be homogeneously and uniformly mixed within the entire plastic matrix, instead of only being located on the surface. As such, the hygienic requirement and mechanical performance requirement of robot arm can be simultaneously met.

Compared to the above-mentioned conventional stainless steel based solutions, such plastic-based solution in the present disclosure may provide a light weight solution with inherent corrosion-resistant ability. Further, compared to the coating-based solutions where the mechanical portion of the robot is still made of a raw material similar to that of a conventional one (such as iron or aluminum), the bulk antimicrobial solution in the present disclosure may effectively avoid the crack and peeling which is mainly caused by the limited lifetime of the functional coatings.

Moreover, such plastic-based structural member enables easy fabrication. For example, in some embodiments, the structural member can be formed from the plastic matrix and the antimicrobial additive and by injection moulding, machining, or 3D printing.

In order to minimize the gap in terms of the mechanical performance between the metal and plastic composites, high mechanical performance plastic material is usually required. Therefore, in some embodiments, the plastic matrix can be made of a fiber reinforced plastic. In an example, the fiber reinforced plastic may have the failure strength of at least 130 MPa and fatigue strength of at least 35 MPa after $10^6$ cycles in the S—N curves (with Al alloy used as a benchmark) to provide an excellent mechanical performance.

In some embodiments, the fiber reinforced plastic can be a long fiber reinforced plastic. Structural members made of long fiber reinforcement show very low creep tendency and enhanced fatigue strength, which is suitable for the robot arms under static and dynamic loading conditions. Normally, the long-glass fiber reinforced plastic display more linear behavior in a tensile test and great elastic deformability.

In some other embodiments, the fiber reinforced plastic can be high fiber content reinforced plastic with a fiber content larger than 30%, or larger than 40%, or even larger than 50%. Fiber reinforced plastic with high fiber content can provide the acceptable strength and module for robot arm application.

Of course, it is to be understood that other types of reinforced plastics, such as short fiber reinforced plastic are also feasible, depending on the mechanical performance requirements or applications of the structural member.

Alternatively, or in addition, in some embodiments, the plastic matrix may be required to have a characteristic of low humidity absorption as the mechanical performance would be reduced by humidity, otherwise. In some embodiment, food contact certified plastic might also be required, especially for food and beverage application.

Antimicrobial additives for plastics material show specific actives that can keep the plastic surface lasting protection from microbes, kill the microbes or inhibits their growth. The additives can be formulated into a concentrated powder, liquid suspension or master batch pellet for different manufacturing process and applications. For example, the antimicrobial additive may take a form of a master batch and manufactured by extruder compounding. The main three types of antimicrobial additives include: (i) metal ion type; (ii) inorganic oxide type, and (iii) organic type.

In some embodiments, the antimicrobial additive may be the metal ion type (also referred to as the first type), which comprises a metal ion including, but not limited to, silver ion and copper ion. Such metal ions can interact with membrane proteins to block respiration and electron transfer, or interact with DNA, proteins and induce reactive oxygen species (ROS) production inside the cell. Take silver ion for example, its features include good thermal stability, broad spectrum antimicrobial ability and safe to use.

Alternatively, or in addition, the metal ion type of antimicrobial additive may further comprises a carrier for coupling with the metal ion. The carrier can include, but not limited to, zeolite or glass. The zeolite or glass is usually used as carrier material for more effective antimicrobial performance. The antimicrobial efficiency of such silver system (that is, metal ion-carrier) additive can reach a level larger than 99%. In this case, most bacterial cannot survive on the surface of plastic with silver system antimicrobial additive.

In some embodiments, the antimicrobial additive may be the inorganic oxide type (also referred to as the second type), which comprises a photo catalyst that can be zinc oxide (ZnO) or titanium dioxide ($TiO_2$). Photo catalyst is defined as substance which is activated by adsorbing a photon and is capable of accelerating a chemical reaction without being consumed. When exposed to ultra violet (UV) light, the photo catalysts interact with oxygen and moisture existing in the environment to produce ROS, which can decompose most microorganisms that are harmful to human body and environment.

As an example, $TiO_2$ is typical photo catalyst with antimicrobial function. Its feature includes broad spectrum activity and targeting non-selective, high performance and everlasting effect, decomposition of germ body and endotoxin, safety and no extra pollution. Especially in the UV environment, the antimicrobial efficiency can be even above 99%. That is to say, almost all of bacterial cannot survive on the surface of plastic with $TiO_2$ system antimicrobial additive. It is particularly suitable for high hygienic level with UV disinfection.

Alternatively, or in addition, the inorganic oxide type of antimicrobial additive may further comprise a metal ion as a doping of the photo catalyst. Typical coupling agent includes, but not limited to silver. Alternatively, or in addition, the inorganic oxide type of antimicrobial additive may further comprises a coupling agent to couple the photo catalyst to the plastic matrix. With the introduction of coupling agent, the interface between the photo catalyst and polymer matrix can be improved. Typical coupling agent includes, but not limited to KH550.

In some embodiments, the antimicrobial additive may be the organic type (also referred to as the third type), which comprises at least one of: quaternary ammonium salt, peptide, low molecular weight agents, and antimicrobial polymers.

It is to be understood that, more than two types of antimicrobial additive can be used together to achieve a more complex antimicrobial additive system, so as to achieve some additional advantageous effects.

Merely by way of example, the first type and the second type may be used together to form an antimicrobial additive system. As discussed above, for example, the photo catalyst comprising the silver as the doping may also be considered as a combination of the first type of the antimicrobial additive (that is, the silver doping) with the second type of the antimicrobial additive (that is, the photo catalyst). In this way, the antimicrobial efficiency of the photo catalyst can be further improved.

Table 1 as below shows the experimental results for both the metal ion type antimicrobial samples (upper half of the table) and the inorganic type antimicrobial sample (lower half of the table) in terms of the antibacterial efficiency. In the shown experimental results, *Escherichia coli* (*E. coli*) is used throughout all tests, and different antimicrobial additive systems are used in different tests.

TABLE 1

| Sample | Additives content | *Escherichia coli* is used in the test | |
|---|---|---|---|
| | | Test standard | Antibacterial efficiency |
| Plastic benchmark | 0 | JIS Z 2801: 2010 | No activity |
| Ag-Glass/Plastic | 1% | | 95% |
| Ag-Zeolite/Plastic | 0.5% | | 79% |
| Ag/Plastic | 2% | | 98% |
| Cu-Glass/Plastic | 5% | | >99% |
| $TiO_2$-KH550/Plastic | 2% | GBT 23763-2009 | >99% |
| $TiO_2$—Ag/Plastic | 1% | | >99% |
| ZnO—Ag/Plastic | 5% | | >99% |
| ZnO-KH550/Plastic | 0.5% | | 98% |

From Table 1, it can be seen that when the content of the antimicrobial additives (for both metal ion type and inorganic oxide type) in the structural member is in a range of 0.5-5 wt %, relatively high antibacterial efficiencies greater than 99% can be achieved. As further illustrated in Table 1, with properly selected antimicrobial additive systems as well as their associated contents, the antibacterial efficiency can be even greater than 99%.

Figure 3:
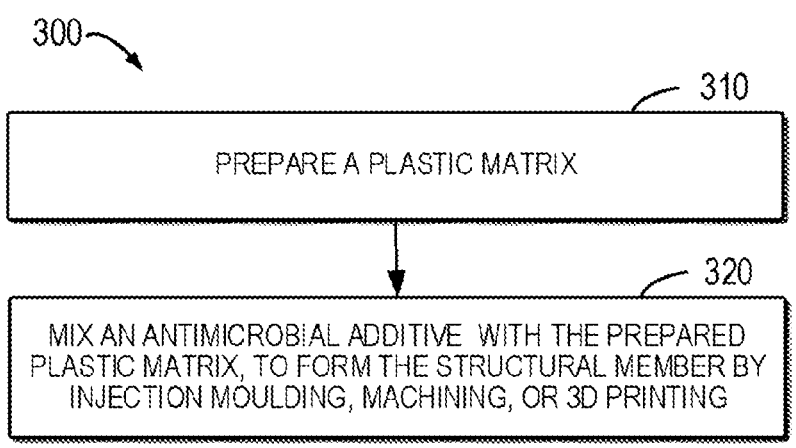
FIG. 3 illustrates a flow chart of a method for manufacturing the structural member a robot as shown in FIG. 2.

FIG. 3 illustrates a flow chart of a method 300 for manufacturing the structural member that is adapted to expose to an environment and bear a mechanical load, as shown in FIG. 2.

At 310, a plastic matrix is prepared. For example, depending on the mechanical requirements or application fields, short fiber reinforced plastic, long fiber reinforced plastic, or a fiber reinforced plastic with a high fiber content larger than 30%, or larger than 40%, or even larger than 50% needs to be prepared accordingly.

At 320, an antimicrobial additive can be mixed with the plastic matrix prepared at 310 to form the structural member by, for example, injection moulding, machining, or 3D printing.

Figure 4:
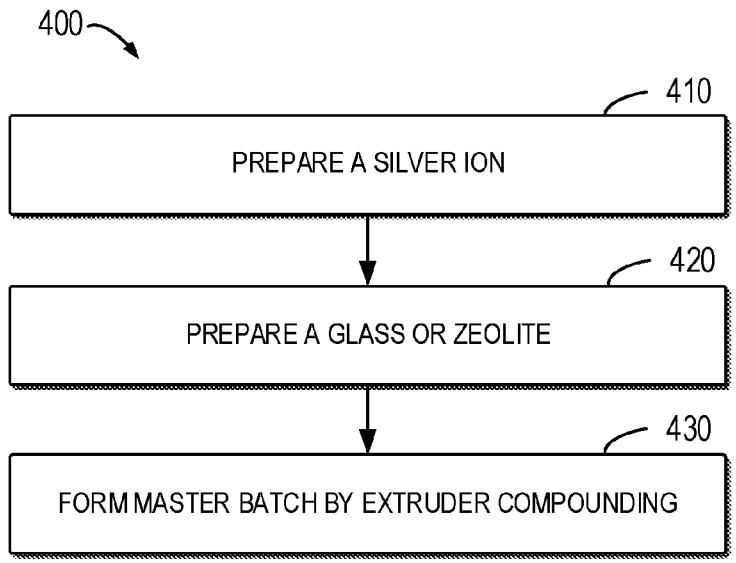
FIG. 4 illustrate a flow chart of a method for forming a metal type of antimicrobial additive in the form a master batch.

In some embodiment, at 320, the antimicrobial additive may take the form of a master batch which may be preformed by extruder compounding, for example. FIG. 4 illustrates a flow chart 400 of a method for forming a metal type of antimicrobial additive in the form the master batch. In this example, at 410, silver ion is selected and prepared as the metal type of antimicrobial additive. At 420, a glass or zeolite is selected and prepared as the carrier for coupling with the silver ion to achieve more effective antimicrobial performance. At 430, the antimicrobial system (silver ion+ glass/zeolite) in the form of master batch can be formed by extruder compounding.

Figure 5:
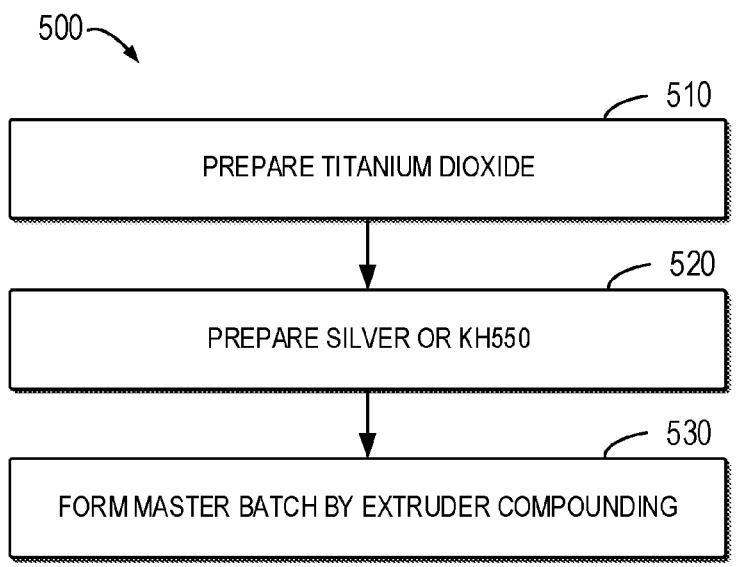
FIG. 5 illustrate a flow chart of a method for forming an inorganic type of antimicrobial additive in the form a master batch.

FIG. 5 illustrates a flow chart 500 of a method for forming an inorganic type of antimicrobial additive in the form a master batch. In this example, at 510, $TiO_2$ is selected and prepared as the inorganic type of antimicrobial additive. At 520, a silver or KH550 is selected and prepared as the doping or coupling agent for $TiO_2$ to improve the antimicrobial efficiency of the photo catalyst. At 530, the antimicrobial system ($TiO_2$+silver/KH550) in the form of master batch can be formed by extruder compounding.

In sum, various embodiments of the present disclosure provide a plastic-based, bulk, antimicrobial structural member of a robot. Compared to conventional solutions, such bulk antimicrobial plastic solution for robot arm can achieve several advantageous such as: long term stability and endurance for antimicrobial function compared to coating solution; easy-to-maintenance (possible simplified cleaning processing and less-frequent cleaning for hygienic application); easy fabrication processing (e.g. colorful design without painting processing); and light weight and possible low cost as metal replacement.

It is to be understood that the above detailed embodiments of the present disclosure are only to exemplify or explain principles of the present disclosure and not to limit the present disclosure. Therefore, any modifications, equivalent alternatives and improvement, etc. without departing from the spirit and scope of the present disclosure shall be included in the scope of protection of the present disclosure. Meanwhile, appended claims of the present disclosure aim to cover all the variations and modifications falling under the scope and boundary of the claims or equivalents of the scope and boundary.

What is claimed is:

1. A structural member of a robot, wherein the structural member is adapted to be exposed to an environment and bear a mechanical load, the structural member comprises:
    a plastic matrix; and
    an antimicrobial additive mixed with the plastic matrix comprising:
        a first antimicrobial additive,
            wherein the first antimicrobial additive is a metal ion antimicrobial additive comprising silver ion and copper ion, and wherein the first antimicrobial additive further comprises a first carrier comprising zeolite and glass, for coupling with the metal ion antimicrobial additive, and
            wherein a content of the first antimicrobial additive in the structural member is in a range of 0.5-5 wt %, and
        a second antimicrobial additive,
            wherein the second antimicrobial additive is an inorganic oxide antimicrobial additive and comprises a photo catalyst comprising zinc oxide and titanium dioxide.

2. The structural member of claim 1, wherein the structural member comprises: an arm, a wrist, a translation axle, or a rotary axle of the robot.

3. The structural member of claim 1, wherein the structural member is formed from the plastic matrix and the antimicrobial additive by injection molding, machining, or 3D printing.

4. The structural member of claim 1, wherein the plastic matrix is made of a fiber reinforced plastic.

5. The structural member of claim 4, wherein the fiber reinforced plastic comprises a fiber content larger than 30 wt %.

6. The structural member of claim 5, wherein the fiber reinforced plastic with the fiber content larger than 30% comprises a fiber content larger than 40%.

7. The structural member of claim 1, wherein the second antimicrobial additive further comprises the metal ion antimicrobial additive as a doping of the photo catalyst.

8. The structural member of claim 1, wherein the second antimicrobial additive further comprises a coupling agent to couple the photo catalyst to the plastic matrix.

9. The structural member of claim 1, wherein a content of the first antimicrobial additive and the second antimicrobial additive in the structural member is in a range of 0.5-5 wt %.

10. The structural member of claim 1, wherein the antimicrobial additive further comprises a third antimicrobial additive, and wherein the third antimicrobial additive is an organic antimicrobial additive and comprises at least one of: quaternary ammonium salt, peptide, and antimicrobial polymers.

11. The structural member of claim 10, wherein a content of the first antimicrobial additive and the third antimicrobial additive in the structural member is in a range of 0.5-5 wt %.

12. A method for manufacturing a structural member of a robot, comprising:
   preparing a plastic matrix; and
   mixing an antimicrobial additive with the plastic matrix to form, by injection molding, machining, or 3D printing, the structural member that is adapted to expose to an environment and bear a mechanical load;
   wherein the antimicrobial additive comprises a first antimicrobial additive, a second antimicrobial additive, and a first carrier,
      wherein the first antimicrobial additive is a first metal ion antimicrobial additive and comprises a metal ion comprising silver ion and copper ion,
      wherein a content of the first antimicrobial additive in the structural member is in a range of 0.5-5 wt %, and
      wherein the first carrier comprises zeolite and glass, for coupling with the metal ion,
      wherein the second antimicrobial additive is an inorganic oxide antimicrobial additive and comprises a photo catalyst comprising zinc oxide and titanium dioxide.

13. The method of claim 12, wherein preparing the plastic matrix comprises:
   preparing the plastic matrix from a fiber reinforced plastic.

14. The method of claim 13, wherein the fiber reinforced plastic comprises a fiber content larger than 30%.

15. The method of claim 14, wherein the fiber reinforced plastic with the fiber content larger than 30% is a fiber reinforced plastic with a fiber content larger than 40%.

16. The method of claim 12, further comprising:
   forming the antimicrobial additive having a form of a master batch by extruder compounding.

17. The method of claim 12, wherein the second antimicrobial additive further comprises a second metal ion as doping of the photo catalyst.

18. The method of claim 12, wherein the second antimicrobial additive further comprises a coupling agent to couple the photo catalyst to the plastic matrix.

19. The method of claim 12, wherein a content of the first antimicrobial additive and the second antimicrobial additive in the structural member is in a range of 0.5-5 wt %.

20. The method of claim 12, wherein the antimicrobial additive further comprises a third antimicrobial additive, and wherein the third antimicrobial additive is an organic type and comprises at least one of: quaternary ammonium salt, peptide, low molecular weight agents, and antimicrobial polymers.

21. The method of claim 20, wherein a content of the first antimicrobial additive and the third antimicrobial additive in the structural member is in a range of 0.5-5 wt %.

22. The method of claim 12, wherein the structural member comprises:
   an arm, a wrist, a translation axle, or a rotary axle of the robot.

23. A robot, comprising:
   a plastic matrix; and
   an antimicrobial additive mixed with the plastic matrix comprising:
      a first antimicrobial additive,
         wherein the first antimicrobial additive is a metal ion antimicrobial additive comprising silver ion and copper ion, and wherein the first antimicrobial additive further comprises a first carrier comprising zeolite and glass, for coupling with the metal ion antimicrobial additive,
         wherein a content of the first antimicrobial additive is in a range of 0.5-5 wt %, and
      a second antimicrobial additive,
         wherein the second antimicrobial additive is an inorganic oxide antimicrobial additive and comprises a photo catalyst comprising zinc oxide and titanium dioxide.

* * * * *